United States Patent [19]

Ellis, Jr. et al.

[11] Patent Number: 5,091,354

[45] Date of Patent: Feb. 25, 1992

[54] ALKANE OXIDATION CATALYSTS

[75] Inventors: Paul E. Ellis, Jr., Downington; James E. Lyons, Wallingford, both of Pa.

[73] Assignee: Sun Refining and Marketing Company, Philadelphia, Pa.

[21] Appl. No.: 550,935

[22] Filed: Jul. 11, 1990

Related U.S. Application Data

[63] Continuation-in-part of Ser. No. 254,750, Oct. 7, 1988, Pat. No. 4,898,989.

[51] Int. Cl.$^5$ .................. B01J 27/24; B01J 27/18; B01J 27/188; B01J 21/06
[52] U.S. Cl. ..................... 502/200; 423/306; 423/376; 502/209; 502/210; 502/211; 502/212; 502/247; 502/254; 502/255; 502/308; 502/309; 502/311; 502/312; 502/350; 502/353; 568/399; 568/910
[58] Field of Search .................. 502/200, 208–212, 502/247, 254, 255; 423/306, 376

[56] References Cited

U.S. PATENT DOCUMENTS

| | | | |
|---|---|---|---|
| 2,608,534 | 8/1952 | Fleck et al. | 502/211 |
| 4,146,574 | 3/1979 | Onada et al. | 423/306 |
| 4,522,934 | 1/1985 | Shum et al. | 502/209 |
| 4,720,474 | 1/1988 | Vasilevskis et al. | 502/201 |
| 4,803,187 | 2/1989 | Lyons et al. | 502/200 |
| 4,853,357 | 8/1989 | Vasilevskis et al. | 502/201 |
| 4,859,798 | 8/1989 | Lyons et al. | 502/200 |
| 4,916,101 | 4/1990 | Lyons et al. | 502/209 |

Primary Examiner—Paul E. Konopka
Attorney, Agent, or Firm—Q. Todd Dickinson; Donald R. Johnson

[57] ABSTRACT

Site-specific, framework substituted heteropolyacid or a polyoxoanion catalysts useful in alkane oxidation processes.

5 Claims, No Drawings

ALKANE OXIDATION CATALYSTS

This application is a continuation in part of Ser. No. 254,750 filed Oct. 7, 1988, now U.S. Pat. No. 4,898,989.

This invention relates to polyoxoanion (POA) or heteropolyacid (HPA) oxidation catalysts which have been promoted or otherwise modified to improve their effectiveness in the oxidation of alkanes.

CROSS-REFERENCE TO RELATED APPLICATIONS

This application is related to our U.S. Pat. Nos. 4,898,989, 4,859,798, and 4,803,187.

BACKGROUND OF THE INVENTION

The use of POAs and HPAs for the catalytic air oxidation of alkanes such as butane is known. [See, for example, M. Ai, Partial Oxidation of n-Butane with Heteropoly Compound-based Catalysts, Proceedings of the 18th International Congress on Catalysis, Berlin, 1984, *Verlag Chemie* Vol. 5, page 475]. In addition our patent U.S. Pat. No. 4,803,187 describes the use of HPAs and POAs in liquid phase oxidation of alkanes; this patent is incorporated herein by reference.

HPAs and POAs, both in general, and those which can be used to prepare the catalysts used in our invention, and their preparation are thoroughly described in *Heteropoly and Isopoly Oxo-metalates*, Pope et al, Springer-Verlag, New York 1983. In order to clarify the terminology used in the art, consider first a specific precursor used in our invention, $H_3PW_{12}O_{40}$. Since the cations in this material are hydrogen, the compound is a heteropolyacid. If the cations are not hydrogen but are metals such as an alkali metal, potassium, sodium, or lithium, or are ammonium, as in $K_3PW_{12}O_{40}$ or $(NH_4)_3PW_{12}O_{40}$, then it is obviously no longer an acid, and is referred to as a polyoxoanion.

As described in Pope, HPAs and POAs are cage-like structures with a primary, generally centrally located atom(s) surrounded by the cage framework which contains a plurality of other metal atoms, the same or different, bonded to oxygen atoms. Since the central atom is different from the other metal atoms, it is described as "hetero." The other metal atoms are transition metals and have oxygen bonding such as

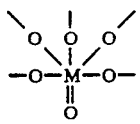

where four of the singly bonded oxygen atoms are bonded to other M atoms in the framework and the fifth is bonded to the central hetero atom.

SUMMARY OF THE INVENTION

Our invention involves HPA and POA catalysts useful in the selective oxidation of alkanes with oxygen at relatively mild conditions (usually under 200° C.) to a product rich in alcohol and with little or no burn of alkane to carbon oxides. Our HPAs and POAs are promoted by the substitution of certain metal atoms in the framework with certain other metal atoms which results in an HPA or POA which differs from a "conventional" HPA or POA.

In our prior U.S. Pat. Nos. 4,803,187 and 4,859,798, we disclosed the use of certain promoted and/or modified HPAs/POAs. In those patents, we described a modification known as "framework substituted" HPAs and POAs wherein one or more of the metal=oxygen units in the cage structure is replaced by a different metal atom resulting in a more active catalyst. Our U.S. Pat. No. 4,898,989 is directed to an improved type of framework substitution wherein three metal atoms in a triangular face in the HPA or POA framework are replaced with three different metals that render the HPA or POA still more active. The framework substitution described in our earlier '187 and '798 patents is a random substitution. The '989 patent discloses how to control the locus of the substitution. The present application relates to certain of the catalyst compositions disclosed in the '989 patent.

Polyoxoanions having a three metal substitution in a triangular face are known. See Finke et al., *J. Amer. Chem. Soc.* 108, p. 2947 (1986) disclosing $(Bu_4N)_4H_3(SiW_9V_3O_{40})$; Domaille and Watunya, *Inoro. Chem.* 25, p. 1239 (1986) disclosing $K_6(PW_9V_3O_{40})$ and its tetrabutylammonium salt; and F. Ortega, Ph.D. Thesis, Georgetown Univ. (1982) disclosing $K_7(SiW_9Fe_3O_{37})$. However, their use in alkane oxidations is not known nor is the superior activity of the catalysts of the present invention disclosed.

DETAILED DESCRIPTION

Our invention deals with improvements to HPAs (and POAs thereof) having the general formula $H_e(X_kM_nO_y)^{-e}$ where X, the central atom is phosphorus, arsenic, zirconium, titanium or silicon, germanium, preferably phosphorus, and subscript k is preferably 1 or 2 but can be as high as 4–5. M is molybdenum, tungsten, or vanadium and n will vary from 5–20, preferably is 12 or 18. Subscript y is usually 40 or 62 but can be as low as 18 or as high as 62. Notation e is the valence of the $(X_kM_nO_y)$ group and will vary from case to case, but e is always the number of H atoms needed to balance the formula. In a preferred precursor HPA, i.e., the HPA which can be improved for use in our invention, $k=1$, $n=12$ and $y=40$ as in $H_3PMo_{12}O_{40}$ and in $K_4PW_{11}VO_{40}$. These and similar HPAs and POAs are shown in the aforesaid Pope reference. Most of our catalysts are of the Keggin structure and its isomers, as described in Pope, but other structures such as the Dawson structure also are suitable.

HPAs are conventionally made by dissolving the metal oxides in the desired proportion in water, adjusting the pH to approximately 1–2 with acid (e.g. HCl) and then evaporating water until the HPA precipitates. If the POA is desired, a salt such as KCl is added and the POA precipitates, without need for the evaporation step. The desired proportion of the metal oxides added will vary somewhat from the theoretical amount required for the desired product, because in the precipitation step they do not precipitate in those exact same ratios. However, this is a matter of routine testing and adjustment. The existence of the HPA structure, i.e., the metal oxygen bonds, is confirmed by their characteristic NMR and/or IR spectra, which, as explained in Pope supra, are now known for the various HPAs.

We have found that the activity of the precursor HPAs described above for the oxidation of alkanes is improved by replacing certain M atoms (and the oxygen atoms doubly bonded to them) with certain transition metals. The M atoms to be replaced are best shown from the following structure

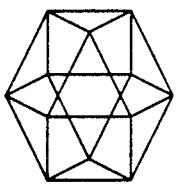

This twelve-cornered polyhedron structure is the metal atom configuration of a typical HPA described above, i.e., each of the above corners is a metal atom.

Between any two metal atoms is an oxygen atom, not shown, and from each metal atom is a doubly bonded oxygen, also not shown, and each of the metal atoms is bonded to an oxygen atom which is bonded to the central metal atom, not shown.

It can be seen from the diagram that eight of the fourteen faces of the above polyhedron are triangular and the other six are four-sided polygons. The M atoms which are replaced, according to our invention are the metal atoms in a triangular face, not just any metal atoms as would happen in a random replacement. The latter is what is disclosed in our earlier two patents described above.

As noted above, a typical HPA precursor of our invention has the formula $H_3PMo_{12}O_{40}$. When three M=O units are replaced with, e.g., Fe, the resulting framework substituted HPA has the formula $H_6PMo_9Fe_3O_{37}$. Thus, the general formula of the HPAs of our invention becomes $$H_e(X_kM_nM'_3O_y)-e$$

where k is 1-5, n is 5-17, preferably 9 or 15 and y is 18-59, preferably 37 or 59.

M' must be iron, chromium, manganese, or ruthenium in at least one instance but otherwise can be zinc or any of the transition metals, namely the Group IV(a)-VIII metals of the periodic table (IUPAC notation). These are Ti, V, Cr, Mn, Fe, Co, Ni, Zr, Nb, Mo, Tc, Ru, Rh, Pd, Hf, Ta, W, Re, Os, Ir, and Pt. Preferably the transition metal is from Group VIII or the first row of Group IV(a)-VII, i.e., Fe, Co, Ni, Ru, Rh, Pd, Os, Ir, Pt (Group VIII) or Ti, V, Cr, Mn (IV(a)-VII first row). The more preferred M' metals are Fe and Ni. Also, and as will be seen below in the examples, the three M' atoms should not be the same. Also, and quite obviously, M'$_3$ must be different than the three M atoms replaced.

The reason why at least one M' must be iron, chromium, manganese or ruthenium is that these four metals seem to provide superior catalyst activity. For example, M'$_3$=Fe$_2$Ni provides a superior catalyst to M'$_3$=V$_3$. Preferably at least two, more preferably all three, M' atoms are from this group of four.

As noted above, the framework substitution procedure described in our earlier patents is adequate for random substitution but will not consistently provide the site specific substitution of the present invention. In order to achieve the latter, the following generalized procedures are employed.

The overall procedure involves the reaction of a trilacunary polyoxoanion with a trimetalacetate, the metals of the latter being those to be inserted into the POA. The framework substituted POA is then converted to the corresponding HPA if desired. The trilacunary, $Na_9(PW_9O_{34})$, for example is prepared by mixing $Na_2WO_4$ and $H_3PO_4$ in the stoichiometric ratio in water at room temperature for 25 minutes and then slowly acidifying with 12N HCl to a final pH of 7.1. The $Na_9PW_9O_{34}$ precipitates and is separated. Other trilacunaries are prepared similarly by known analogous procedures.

It is apparent from the above that the $PW_9O_{34}$ in the trilacunary POA represents the formal removal of three O—W=O units from the polyoxoanion and not merely W=O described for the framework substituted HPA/POA of our two earlier patents. The singly bonded oxygen in the O—W=O is reinserted when an O—M' unit is inserted so that the overall effect is the replacement of three M=O units with three M' units; thus changing the number of framework oxygen atoms from 40 to 37.

The trimetal acetates have the general formula $M_3O(CH_3COO)_6(H_2O)_3$ where M is a transition metal or zinc such as $Fe_2NiO(CH_3COO)_6(H_2O)_3$. They are prepared, e.g., by reaction of appropriate salts. Thus the above diiron-nickel compound is prepared by mixing sodium acetate, iron nitrate, and nickel nitrate in aqueous acetic acid at room temperature and separating the precipitate. See Blake, et al. *J. Chem. Soc. Dalton Trans.*, p. 2509 (1985) and Uemura, et al. *J. Chem. Soc. Dalton Trans.*, p. 2565 (1973).

Once the precursors are prepared, the framework substituted HPA/POA is formed by reacting them together. For example trilacunary polyoxoanion $Na_9(PW_9O_{34})$ is dissolved in a pH 6, buffered KOAc/HOAc solution (OAc=acetate). Then an equimolar amount of the trimetal acetate, e.g., $Fe_2NiO(OAc)_6(H_2O)_3$ dissolved in water, is added. After initial mixing, the mixture is stirred for one hour at 50° C. and then cooled to room temperature. KCl is added to precipitate the product $K_7(PW_9Fe_2NiO_{37})$. Various preparatory methods are described in Finke et al. *JACS* 108, p. 2947 (1986), F. Ortega, op. cit., and Domaille and Watunga, op. cit.

The polyoxoanion salt can be readily converted to the acid form if desired. This is done by reacting an aqueous solution of the salt, e.g., $K_7PW_9Fe_2NiO_{37}$ at 50° C. for 15 minutes with an aqueous solution containing an excess of tetrabutylammonium bromide. Upon refrigeration at 4° C. overnight, the organic salt, $(n-C_4N)_7PW_9Fe_2NiO_{37}$ crystallizes in 70% yield. The organic salt is filtered off and pyrolyzed at 500° C. for 1 hr. It turns into the black solid $H_7PW_9Fe_2NiO_{37}$, as confirmed by IR.

The existence of the framework substituted HPAs or POAs of our invention is confirmed by IR and elemental analysis in known manner.

By way of example, using the preparative procedures described above, the catalysts of our invention shown in Table I, as well as the potassium, tetrabutyl ammonium and hydrogen forms of the following framework substituted anions of the catalysts of the invention are prepared:

$(PW_9Fe_2NiO_{37})^{-7}$ $(PW_9Fe_2ZnO_{37})^{-7}$ $(PW_9Fe_2PdO_{37})^{-7}$ $(PW_9Fe_2CrO_{37})^{-7}$ $(PW_9Fe_2MnO_{37})^{-7}$ $(PW_9Fe_2^{+3}Fe^{+2}O_{37})^{-7}$

Our earlier patents, referred to above, disclosed the promotion of HPA/POAs with V, Ti, Nb, Re, or azide for use in alkane oxidation. In like manner, the catalysts of the present invention may be similarly promoted to gain further advantageous results.

The oxidation of alkanes with our catalysts is usually carried out in the presence of a solvent. It should be an unreactive polar solvent such as water, acetic acid, acetonitrile, benzonitrile, mixtures of water and acetic acid with chlorobenzenes, and the like. These solvents will yield a single phase homogeneous system although this is not always critical. Some solvents, such as benzene, are useful with HPAs but not POAs because of the difference in solubility.

The oxidation is carried out at 50°–350° C., in many cases 50°–200° C., more preferably 125°–175° C., and the low temperature is an advantage of the invention. The pressure is 0–5000 psig, and preferably is high enough to maintain the liquid phase, although this is not critical. Reaction time is 0.1–10 hours depending on conditions and is readily selected by the skilled worker. The amount of catalyst employed is generally 0.0001–1.0 mmoles catalyst per mole of reactant, preferably 0.001–0.1 but is always a catalytically effective amount.

The alkane starting materials include straight and branched-chain compounds having from about 1–20 carbon atoms, preferably 1–10 carbon atoms, more preferably 1–5, such as methane, ethane, propane, n-butane, isobutane, n-pentane, n-hexane, 2-methylpentane, 3-methylpentane, heptane, 2-methylheptane, 3-methylheptane and the like, as well as cycloalkanes having from about 5–20 carbon atoms, preferably 5–10 carbon atoms, such as cyclopentane, cyclohexane, cycloheptane, cyclooctane, and the like. These compounds, if desired, may be substituted with various moieties, although care should be taken to exclude substituents which will adversely affect the activity of the catalyst.

As noted above, our process is highly selective for alcohols and extremely selective for alcohols and ketones, selectivity being defined a the mole percentage of the alkane reacted which is converted to the desired product. In our process the selectivity to alcohol is usually over 40%, often over 60%, and in some cases over 80%. The selectivity to alcohol and ketone is usually over 90%, frequently over 95%, a truly outstanding result. Small amounts of acids are sometimes formed. The amount of carbon oxides formed is generally under 10%, usually less than 5% and is often under 2%, the percentages being expressed as the mole percent yield of carbon oxides based on the reacted alkane.

Table I shows the use of our catalysts in the liquid phase oxidation of propane. The procedure varied slightly in the various runs but is typically as follows:

The propane (1.36 moles) is dissolved in 38 g. of acetonitrile containing the catalyst and the reaction mixture pressured to 100–2000 psig with air or oxygen. The oxidation employed 0.0008–0.050 mmole catalyst per mole of propane, the actual amount being shown after the catalyst formula. The reaction is carried out at 80°–200° C. for 1–10 hours after which the reaction mixture is analyzed. In the table below, TON/hr (turnovers/hr) is the moles of product produced per hour per mole of catalyst used. The products are isopropyl alcohol and acetone; traces of isopropyl acetate by-product is also formed. Selectivity of a product, e.g., IPA, is the moles of IPA produced times 100 divided by the total moles of liquid product produced.

TABLE I

| Run | Catalyst | Amt. Cat-mM. | Temp.-°C. | Time Hrs. | TON/Hr. | Selectivity IPA | Selectivity Acetone |
|---|---|---|---|---|---|---|---|
| A | None | — | 150 | 3 | — | | |
| B | $H_3PW_{12}O_{40}$ | .030 | 150 | 3 | 47 | 45 | 53 |
| 1 | $H_6PW_9Fe_3O_{37}$ | .005 | 150 | 3 | 748 | 39 | 60 |
| 2 | $H_6PW_9Fe_3O_{37}\cdot NaN_3$ | .005 | 150 | 3 | 1048 | 58 | 39 |
| 3 | $H_6PW_9Fe_3O_{37}\cdot NaN_3$ | .0008 | 150 | 3 | 2702 | 36 | 59 |
| 4 | $H_6PW_9Fe_3O_{37}\cdot NaN_3$ | .0008 | 150 | 1.5 | 2260 | 33 | 65 |
| 5 | $H_6PW_9Cr_3O_{37}$ | .0008 | 150 | 3 | 1491 | 32 | 68 |
| 6 | $H_7PW_9Fe_2NiO_{37}\cdot NaN_3$ | .0008 | 164 | 3 | 12340 | 46 | 54 |
| 7 | $H_7PW_9Fe_2NiO_{37}\cdot NaN_3$ | .0008 | 157 | 3 | 8564 | 41 | 58 |
| 8–9 | $H_7PW_9Fe_2NiO_{37}\cdot NaN_3$ | .0008 | 150 | 3 | 3243* | 36 | 63 |
| 10 | $H_7PW_9Fe_2NiO_{37}\cdot NaN_3$ | .0016 | 150 | 3 | 2423 | 40 | 59 |
| 11 | $H_7PW_9Fe_2NiO_{37}\cdot NaN_3$ | .0008 | 125 | 3 | — | — | — |
| 12–13 | $H_7PW_9Fe_2MnO_{37}\cdot NaN_3$ | .0008 | 150 | 3 | 1857* | 39 | 60 |
| 14 | $H_7PW_9Fe_2CoO_{37}\cdot NaN_3$ | .0008 | 150 | 3 | 1096 | 41 | 59 |
| 15–17 | $H_7PW_9Fe_2ZnO_{37}\cdot NaN_3$ | .0008 | 150 | 3 | 1881* | 39 | 60 |
| 18 | $H_6PW_9Cr_3O_{37}\cdot NaN_3$ | .0008 | 150 | 3 | 1849 | 34 | 66 |

*Average of the runs indicated

Runs A and B are controls.

Runs 1 and 5 show the beneficial effect achieved by the triangular framework substitution of iron and chromium respectively.

Runs 2, 3, and 4 show the use of the catalyst of Run 1 further promoted with azide.

Runs 6–11 show the use of diiron-nickel catalyst further promoted with azide.

Runs 12–13 show the use of diiron-manganese catalyst further promoted with azide.

Runs 14 show the use of diiron-cobalt catalyst further promoted with azide.

Runs 15–17 show the use of diiron-zinc catalyst further promote with azide.

Run 18 shows the use of the catalyst of Run 5 further promoted with azide.

The invention claimed is:

1. In an alkane oxidaton catalyst comprising a heteropolyacid having the formula (I) $H_e(X_kM_nO_y)^{-e}$ where x is silicon or phosphorus, M is molybdenum, tungsten, vanadium, or combinations thereof, k is 1–5, n is 5–20, and y is 18–62, or polyoxoanions thereof, the improvement which comprises replacing three atoms of M with three different metal atoms, M', to yield a catalyst having the formula (II) $H_e(X_kM_nM'_3O_y)^{-e}$ where k and M are as above, n is 5–17, y is 18–59, where two atoms of M' are selected from the group consisting of iron, chromium, manganese and ruthenium, and the third atom is different from said other two atoms and is selected from the group consisting of transition metals, where not more than two of the three M' atoms are the same, and wherein M' is free of double-bonded oxygen atoms and each M' atom is bonded through oxygen to another M' atom; or polyoxoanions thereof.

2. Catalyst according to claim 1 wherein said third atom of M' is selected from the group consisting of Group IV(a)–VII, first row, and Group VIII.

3. Catalyst according to claim 1 wherein at least two of the M' atoms are iron.

4. Catalyst according to claim 2 wherein at least two of the M' atoms are iron.

5. Catalyst according to one of claims 1–4 wherein the catalyst is further promoted with azide.

* * * * *